US006488937B1

(12) United States Patent
Smits

(10) Patent No.: US 6,488,937 B1
(45) Date of Patent: Dec. 3, 2002

(54) ALLERGY TREATMENT METHOD USING A RAPID IMMUNOTHERAPY PROTOCOL

(76) Inventor: William Smits, 6409 Post Rd., Fort Wayne, IN (US) 46814

( * ) Notice: Subject to any disclaimer, the term of this patent is extended or adjusted under 35 U.S.C. 154(b) by 69 days.

(21) Appl. No.: 09/644,719

(22) Filed: Aug. 23, 2000

(51) Int. Cl.$^7$ .................. A61K 49/00; A61K 49/14; A61K 39/35; A61K 31/56
(52) U.S. Cl. .............. 424/275.1; 514/825; 514/172; 514/169
(58) Field of Search ............ 424/275.1; 514/825

(56) References Cited

PUBLICATIONS

Portnoy et al, Ann Allergy 73(5): 409–18; Nov. 1994, Abstract.*
Lack et al. Rush immunotherapy results in allergen–specific alterations in lymphocyte function and interferon–gamma production in CD4+ T cells, 1997 J. of Allergy and Clinical Immunology 99(4): 530–538.*
Sharkey et al. Rush immunotherapy: experience with a one–day schedule, Feb. 1996, Ann Allergy Asthma Immunol 76: 175–180.*
Thien et al. Leukotriene antagonists. Do they offer new hope for asthmatics? Jun. 2000, Aust Fam Physician 29(6): 547–51.*
Gans et al. Loratadine (Claritin) in Drug Information Handbook 2nd edition, pp. 551–552; 1995.*

* cited by examiner

*Primary Examiner*—Christina Chan
*Assistant Examiner*—Phuong N. Huynh
(74) *Attorney, Agent, or Firm*—Randall J. Knuth

(57) ABSTRACT

A method of treating a patient sensitive to an allergen includes a desensitizing rapid immunotherapy protocol of administering to the patient a series of gradually increasing doses of a composition comprising the allergen at intervals of about 15 minutes for a duration of less than about 120 minutes, and preferably less than about 90 minutes. A pretreatment protocol administers to the patient a therapeutically effective amount of at least one composition that is effective in reducing a sensitivity of the patient to an asthma associated allergenic reaction.

36 Claims, No Drawings

ALLERGY TREATMENT METHOD USING A RAPID IMMUNOTHERAPY PROTOCOL

BACKGROUND OF THE INVENTION

1. Field of the Invention

The present invention relates to a treatment protocol for administering rapid immunotherapy, and, more particularly, to a method of treating a patient having an immediate hypersensitivity to an allergen using an accelerated rapid immunotherapy schedule, in combination with a method of pretreating such patient prior to receiving the accelerated immunotherapy.

2. Description of the Related Art

Conventional immunotherapy has been found generally effective in the treatment of allergic rhinitis, allergic asthma, chronic sinusitis, and associated headaches. However, disadvantages include poor compliance, delayed efficacy, and patient frustration. Various medical practices have therefore turned their attention towards the use of rush immunotherapy or rapid desensitization because it offers the potential of rapid response, improved compliance, and cost effectiveness.

However, the use in rush immunotherapy of higher antigen dosage levels at accelerated injection schedule intervals is a significant consideration in terms of its impact or responsibility in causing systemic reactions in the patient.

In typical desensitization treatment, it is typically necessary for the patient to have injections very frequently, e.g., initially every two or three days, gradually reducing to once every two or three weeks. This is not only a time-consuming and inconvenient procedure that poses an obstacle to full compliance, but is also very complex due to the need to carefully monitor and control the administered dose of allergen. The potential for allergic reactions such as hives, asthma, and, in some extreme cases, anaphylactic shock, makes desensitization difficult to successfully implement.

SUMMARY OF THE INVENTION

According to the present invention, there is provided a method of treating a patient having an immediate hypersensitivity to allergens of the type that may produce systemic responses such as anaphylactic shock reactions. In accordance with the treatment method, a therapeutically effective desensitizing amount of the allergen is administered to the patient according to a rush or rapid immunotherapy protocol having an accelerated schedule. In one form, the treatment protocol involves administering to the patient gradually increasing doses of the allergen at selected time intervals over a duration of less than about 120 minutes, resulting in a treatment method that when combined with a subsequent observation period lasts less than half a day.

In a preferred form, the allergen is administered at fifteen minute intervals according to a dosing schedule that involves a sequence of six injections effective in advancing the allergic patient to an immunizing or maintenance dose of allergen. For example, such dosing schedule may consist of 0.025 cc of a 1:100,000 allergen dilution, 0.25cc of a 1:100,000 dilution, 0.025 cc of a 1:10,000 dilution, 0.25 cc of a 1:10,000 dilution, 0.025 cc of a 1:1000 dilution, and 0.25 cc of a 1:1000 dilution.

In this application, the ratios and volumes may be altered as may come to be known in the art and still stay within the scope of the invention. Alterations of the ratio and volume dosage may be varied in view of patient needs, allergen sensitivity, and allergen manufacturing and availability.

According to another aspect of the present invention, there is provided a method for pretreating the patient prior to receiving the foregoing rapid immunotherapy treatment protocol. According to the method, a pretreatment protocol is performed which involves administering to the patient prednisone (or any other suitable corticosteroid) and at least one of an $H_1$ histamine antagonist and/or an $H_2$ histamine antagonist. The $H_1$ histamine antagonist may be selected from the group consisting of Claritin™, Seldane™, Zyrtec™, and Allegra™, or other similar medication while the $H_2$ histamine antagonist may be selected from the group consisting of Zantac™, Pepcid™, and Tagamet™, or other similar medication. Such similar medication may be generic forms of the groups or other similar physiological active compounds.

In a preferred form, this premedication regimen is combined with the administration of a therapeutically effective amount of at least one composition which is effective in reducing a sensitivity of the patient to an asthma associated allergenic reaction or simply an allergenic reaction. For example, to control the sensitivity of the patient to an asthma-related allergen, the patient may be administered an inhaled corticosteroid and/or the drug Singular™, which is a trade name of the generic drug leukotriene.

The invention, in one form thereof, is directed to a method of treating a patient sensitive to an allergen or allergens, comprising administering to the patient a therapeutically effective desensitizing amount of a composition comprising the allergen or allergens over a duration of less than about 120 minutes. The treatment method is preferably conducted according to a rapid immunotherapy protocol.

The method, in a preferred form, further includes a pretreatment protocol of administering to the patient prednisone and at least one of an $H_1$ histamine antagonist and/or an $H_2$ histamine antagonist. The $H_1$ histamine antagonist is preferably selected from the group consisting of Claritin™, Seldane™, Zyrtec™, and Allegra™, while the $H_2$ histamine antagonist is preferably selected from the group consisting of Zantac™, Pepcid™, and Tagamet™. Other equivalent physiological active substitutes may be substituted into the $H_1$ and $H_2$ groups.

The pretreatment protocol further includes administering to the patient a therapeutically effective amount of at least one composition effective in reducing a sensitivity of the patient to an asthma associated allergenic reaction. For example, the patient may be administered at least one of a corticosteroid (oral or inhaled) and a Leukotriene antagonist such as Singular™, Accolade™, or Zyflo™.

According to the rush immunotherapy, rapid desensitization, or rapid allergen vaccination protocol of the treatment method, the administration of the allergen amount further comprises administering to the patient at selected intervals gradually increasing doses of the allergen. In a preferred form, each selected interval is about fifteen minutes.

In a more preferred form, the intervaled administration of allergen occurs in accordance with a dosing schedule consisting essentially of: (i) about 0.025 cc of about a 1:100,000 allergen dilution, (ii) about 0.25 cc of about a 1:100,000 dilution, (iii) about 0.025 cc of about a 1:10,000 dilution, (iv) about 0.25 cc of about a 1:10,000 dilution, (v) about 0.025 cc of about a 1:1000 dilution, and (vi) about 0.25 cc of about a 1:1000 dilution.

The invention, in another form thereof, is directed to a method of treating a patient sensitive to an allergen, comprising a protocol of administering to the patient a series of gradually increasing doses of a composition comprising the allergen at selected intervals for a duration of less than about 120 minutes.

In a preferred form, each selected interval is about fifteen minutes. Additionally, the dilution level of allergen within each dosage is preferably within the range from between about 1:150,000 to about 1:50,000 to between about 1:1500 to about 1:500. The amount of the allergen composition administered to the patient is therapeutically effective in desensitizing the patient against the allergen.

The method, in a preferred form, further includes a pretreatment protocol of administering to the patient prednisone and at least one of an Hi histamine antagonist and/or an $H_2$ histamine antagonist. Additionally, the pretreatment protocol further includes administering to the patient a therapeutically effective amount of at least one composition effective in reducing a sensitivity of the patient to an asthma associated allergenic reaction. For example, the patient may be administered at least one of a corticosteroid and the drug Singular™.

The invention, in another form thereof, is directed to a method of treating a patient sensitive to an allergen, comprising a protocol of administering to the patient a series of gradually increasing doses of a composition comprising the allergen at intervals of about 15 minutes for a duration of less than about 120 minutes, and, more preferably, less than about 90 minutes.

In a preferred form, the dilution level of allergen within each dosage is within the range from between about 1:150,000 to about 1:50,000 to between about 1:1500 to about 1:500. More specifically, the protocol is preferably defined by a dosing schedule consisting essentially of: (i) about 0.025 cc of about a 1:100,000 allergen dilution, (ii) about 0.25 cc of about a 1:100,000 dilution, (iii) about 0.0 25 cc of about a 1:10,000 dilution, (iv) about 0.25 cc of about a 1:10,000 dilution, (v) about 0.025 cc of about a 1:1000 dilution, and (vi) about 0.25 cc of about a 1:1000 dilution.

The method, in a preferred form, further includes a pretreatment protocol of administering to the patient prednisone and at least one of an $H_1$ histamine antagonist and/or an $H_2$ histamine antagonist. Additionally, the pretreatment protocol further includes administering to the patient a therapeutically effective amount of at least one composition effective in reducing a sensitivity of the patient to an asthma associated allergenic reaction. For example, the patient may be administered at least one of a corticosteroid (oral or inhaled) and a Leukotriene antagonist such as Singular™, Accolade™, Zyflo™, other zafirlukusts, or other montelukasts.

The invention, in another form thereof, encompasses the method for the treatment of an allergic condition by means of desensitization therapy by administering to a subject gradually increasing doses of a causative agent, wherein the improvement comprises such administration of the causative agent at intervals of between about 10 to 20 minutes for a duration of less than about 120 minutes, using at each interval a dosage of the causative agent within the range of from between about 1:150,000 to about 1:50,000 to between about 1:1500 to about 1:500.

The invention, in yet another form thereof, is directed to a method of pretreating a patient prior to receiving desensitizing rapid immunotherapy. The pretreatment method comprises, in combination, the steps of administering to the patient prednisone and at least one of an $H_1$ histamine antagonist and an $H_2$ histamine antagonist, and administering to the patient a therapeutically effective amount of at least one composition effective in reducing the sensitivity of the patient to an asthma associated allergenic reaction occurrable during and/or after reception of the desensitizing rapid immunotherapy.

In a preferred form, the at least one composition which is administered to reduce the sensitivity of the patient to an asthma associated allergenic reaction includes at least one of a corticosteroid and a leukotriene antagonist, Singular™.

The invention, in yet another form thereof, is directed to a method of pretreating a patient prior to receiving desensitizing rapid immunotherapy. The pretreatment method comprises, in combination, the steps of administering to the patient prednisone and at least one of an $H_1$ histamine antagonist and an $H_2$ histamine antagonist, and administering to the patient at least one of a corticosteroid and a leukotriene antagonist, Singular™.

One advantage of the present invention is that the protocol for administering allergen to the patient according to a rapid immunotherapy procedure can be successfully accomplished in less than 120 minutes, and may be reduced further to less than 90 minutes (e.g., 75 minutes with six injections spaced at 15 minute intervals), thereby improving compliance.

Another advantage of the present invention is that the rate of systemic reactions in patients can be significantly reduced relative to conventional rush immunotherapies by implementing a pretreatment protocol that administers to the patient a therapeutically effective amount of at least one composition which is effective in reducing the sensitivity of the patient to an asthma associated allergenic reaction that may occur during and/or after reception of the desensitizing rapid immunotherapy.

The exemplifications set out herein illustrate preferred embodiments of the invention, and such exemplifications are not to be construed as limiting the scope of the invention in any manner.

DETAILED DESCRIPTION OF THE INVENTION

A treatment method has been developed that is ordered towards providing therapeutic assistance to patients suffering from acute or immediate hypersensitivity to various allergens. By way of background, immediate hypersensitivity (or anaphylactic response) is a form of allergic reaction which develops very quickly, i.e., within seconds or minutes of exposure of the patient to the causative allergen. As used herein, and conventionally understood, the term "allergen" relates to a specific subclass of antigen which can trigger immediate hypersensitivity, which is mediated by IgE antibodies made by B lymphocytes.

In non-allergic patients, there is no IgE antibody of clinical relevance; however, in a person suffering with allergic diseases, IgE antibody mediates immediate hypersensitivity by sensitizing mast cells that are abundant in the skin, lymphoid organs, membranes of the eye, nose and mouth, and the respiratory tree and intestines. Mast cells have surface receptors for IgE, and the IgE antibodies in allergy-suffering patients become bound to them. When the bound IgE is subsequently contacted by the appropriate allergen, the mast cell is caused to degranulate and to release various substances called bioactive mediators, such as histamine, into the surrounding tissue.

It is the biologic activity of the substances that is responsible for the clinical symptoms typical of immediate hypersensitivity, namely, contraction of smooth muscle in the airways or the intestines, the dilation of small blood vessels and the increase in their permeability to water and plasma proteins, the secretion of thick sticky mucus, and, in the skin, redness, swelling and the stimulation of nerve endings that results in itching or pain.

According to the present invention, a treatment method is provided that encompasses a form of treatment conventionally known in various equivalent alternative forms as rapid desensitization, rapid allergen immunotherapy, rapid allergen vaccination, and rapid or rush immunotherapy. In broad terms, this procedure aims to advance an allergic patient to an immunizing or maintenance dose of extract (i.e., allergen) by administering a series of injections (or via another suitable carrier) of increasing doses of the allergen at frequent intervals. If successful, the patient will exhibit an improved resistance to the allergen, possibly even presenting a total non-reactivity to any subsequent allergen exposure. Conventional rush or rapid desensitization procedures typically take place over a period of one to two days and up to several days and weeks.

According to the present invention, an accelerated rapid immunotherapy protocol has been provided that administers the gradually increasing doses of allergen over a period of less than a few hours and yet achieves a rate of systemic reaction during or following treatment that is dramatically less than that demonstrated by conventional allergen immunotherapies which take much longer.

In accordance with one embodiment of the present invention, a method of treating a patient sensitive to an allergen includes a protocol of administering to the patient a therapeutically effective amount of a composition comprising the allergen over a duration of less than about 120 minutes, and, more preferably, less than about 90 minutes. The protocol is performed according to a rapid immunotherapy protocol in which progressively increasing doses of the allergen are administered at selected intervals, such as 10 to 20 minutes. The protocol is developed with a view towards enabling the patient to reach and/or advance to a maintenance dose within the allocated time frame.

In a preferred form, the treatment protocol employs a dilution level for each allergen dosage that is within the range from between about 1:150,000 to about 1:50,000 to between about 1:1500 to about 1:500. In a more preferred form, the allergen doses are administered at about 15 minute intervals according to the following dosage schedule:

| INTERVAL TIME (approx.) | DOSAGE (approx.) |
| --- | --- |
| 0 | 1:150,000 to 1:50,000 |
| 15 | 1:150,000 to 1:50,000 |
| 30 | 1:15,000 to 1:5,000 |
| 45 | 1:15,000 to 1:5,000 |
| 60 | 1:1500 to 1:500 |
| 75 | 1:1500 to 1:500 |

Optional dosages of between about 1:150 to 1:50 may be administered at 90 minutes and 105 minutes.

It should be understood that the manner of delivering the allergen dosages may encompass any suitable route (e.g., oral or injection) and employ any pharmaceutically acceptable carrier as well understood by those skilled in the art. Additionally, the times and dosage levels indicated above should be understood as forming guidelines that the skilled artisan may use to make adjustments thereto within the scope of the present invention. Other aspects of performing the rapid immunotherapy procedure are well within the routine understanding and practice of those skilled in the art. The ratios, volumes, and selected allergen may be changed by the skilled artisan.

An examination and evaluation study was performed which conducted two separate half-day schedules for desensitizing and observing 311 patients according to the present invention. All patients exhibited positive percutaneous skin tests to perennial and seasonal inhalant allergens. The targeted final dose ranged from about 0.1 cc to about 0.5 cc of about a 1:1000 dilution of aqueous and glycerinated extracts manufactured by ALK and Greer Laboratories. Most patients were then continued onto higher doses by resuming a conventional immunotherapy schedule. Patients ranged from 1½ to 68 years of age. Diagnoses included allergic rhinitis (92%), asthma (51%), and chronic sinusitis (63%). Most patients also had associated headaches.

The following table illustrates the dosing schedule used in the foregoing study, using about 15 minute intervals for administering the allergen dosage.

| INTERVAL TIME (approx.) | DOSAGE (approx.) | AMOUNT (vol.) (approx.) |
| --- | --- | --- |
| 0 min. | 1:100,000 | 0.025 cc |
| 15 min. | 1:100,000 | 0.25 cc |
| 30 min. | 1:10,000 | 0.025 cc |
| 45 min. | 1:10,000 | 0.25 cc |
| 60 min. | 1:1000 | 0.025 cc |
| 75 min. | 1:1000 | 0.25 cc |
| 90 min. | 1:100 | 0.025 cc |
| 105 min. | 1:100 | 0.1 cc |

The dosages at 90 minutes and 105 minutes are optional. It should be understood that the indicated volumetric quantities applicable to each dosage may be suitably adjusted in a known manner to facilitate or otherwise adapt the immunotherapy protocol based upon the patient reaction or condition or in response to other factors well understood by those skilled in the art. Dosage ratios may be varied within the scope of the present invention. One reason the ratios may need to be changed may be sensitivity of the patient to the allergen (e.g., 1:1,000,000,000, 1:1,000,000) to create an effective treatment for very allergic patients.

The foregoing dosage schedule would be used in conjunction with administering the allergen amount into one arm of the patient, for example. A substantially identical schedule would be used to administer another allergen amount into the other arm. Preferably, different allergen types would be used to enable rapid desensitization involving two different antigens within the same day. The two desensitization regimens may be performed concurrently with one another (as in the foregoing study) or may be conducted in serial manner with one protocol following the other, preferably within the same day.

Follow-up observations of the patients involved in the study revealed that eleven patients (3.5%) experienced a mild systemic reaction. Significantly, these documented systemic reactions occurred less frequently with the treatment protocol disclosed herein and used a lower targeted final dose than previously described in the art. All of the patients responded to subcutaneous epinephrine and/or nebulized albuterol and were deemed fit to return home. None of the patients experienced true anaphylactic shock. These clinical results confirm that maintenance immunotherapy according to the present invention can be reached quickly, safely, effectively and with improved compliance.

In accordance with another embodiment of the present invention, a pretreatment method is provided for use in combination with the treatment protocol described above. The pretreatment method is performed on the patient prior to receiving rapid immunotherapy in the manner described above.

According to one aspect of the pretreatment method, there is provided a protocol or regimen of administering to the patient prednisone (or any other suitable corticosteroid) and at least one of an $H_1$ histamine antagonist and an $H_2$ histamine antagonist. The $H_1$ histamine antagonist may be selected from the group comprising Claritin™ (Loratadine), Seldane™ (Terfenadine), Zyrtec™ (Cetirizine hydrochloride), and Allegra™ (Fexofenadine hydrochloride), for example, while the $H_2$ histamine antagonist may be selected from the group including Zantac™ (Ranitidine hydrochloride), Pepcid™ (Famotidine), and Tagamet™ (Cimetidine), where the associated generic drug name is indicated in parentheses. However, these individual drug types should not be considered in limitation of the present invention as it should be apparent that other suitable anti-histamine or histamine-blocking agents may be used. Additionally, any suitable manner known to those skilled in the art may be used to prepare and administer this premeditation regimen.

It was observed that the efficacy of the rapid immunotherapy protocol (as measured in part by the number and degree of systemic reactions) tended to correlate roughly with the extent of pretreatment that was directed towards reducing or eliminating a sensitivity of the patient to an asthma associated allergenic reaction, such as might occur during and/or after the immunotherapy protocol. Accordingly, the foregoing pretreatment method is enhanced by administering to the patient a therapeutically effective amount of at least one composition which is effective in reducing the sensitivity of the patient to an asthma associated allergenic reaction. For example, the patient may be administered a corticosteroid (oral or inhaled), and a leukotriene medication such as Singular™, Accolade™, Zyflo™, or a combination thereof. Additional asthma medications may also be used.

By controlling this vulnerability or susceptibility to an asthma-related allergenic reaction, it was found that the rate of systemic reactions was capable of being further reduced. The administration of this anti-asthma medication as part of the pretreatment protocol is preferably done in combination with the first premedication regimen discussed above. Notably, the invention does not use antacids as part of the pretreatment protocol.

In the study mentioned above, 107 patients received premedication with prednisone (60 mg daily for adults and 2 mg/kg for children) and $H_1$ antihistamine (Claritin™, Seldane™, Zyrtec™, or Allegra™), for three days prior to receiving rapid desensitization. Additionally, 204 patients received a premedication regimen of prednisone in combination with both $H_1$ and $H_2$ blockade (Zantac™, Pepcid™, or Tagamet™) and Singular™ with a dosage level of approximately 4 to 20 mg.

While this invention has been described as having a preferred methodology and design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of treating a patient sensitive to an allergen, comprising administering to said patient a therapeutically effective desensitizing amount of a composition comprising said allergen at intervals between 10 to 20 minutes over a duration of less than about 120 minutes according to a rapid immunotherapy protocol.

2. The method as recited in claim 1, further comprises a pretreatment protocol of administering to said patient a therapeutically effective amount of at least one composition effective in reducing a sensitivity of said patient to an asthma associated allergenic reaction wherein the composition comprises a corticosteroid and at least one of $H_1$ histamine antagonist and $H_2$ histamine antagonist.

3. The method as recited in claim 2, wherein said pretreatment protocol further comprising administering to said patient at least one of the corticosteroid and the leukotriene antagonist.

4. The method as recited in claim 1, wherein the administration of said allergen amount comprises administering to said patient at selected intervals gradually increasing doses of said allergen.

5. The method as recited in claim 4, wherein each selected interval being about fifteen minutes.

6. The method as recited in claim 1, wherein the intervaled administration of allergen occurring in accordance with a dosing schedule consisting essentially of:
    (i) a dosage having about a 1:100,000 allergen dilution level,
    (ii) a dosage having about a 1:100,000 allergen dilution level,
    (iii) a dosage having about a 1:10,000 allergen dilution level,
    (iv) a dosage having about a 1:10,000 allergen dilution level,
    (v) a dosage having about a 1:1000 allergen dilution level, and
    (vi) a dosage having about a 1:1000 allergen dilution level.

7. The method as recited in claim 1, wherein each allergen dosage having a dilution level within the range of from between about 1:150,000 to about 1:50,000 to between about 1:1500 to about 1:500.

8. The method as recited in claim 7, further comprises a pretreatment protocol of administering to said patient a therapeutically effective amount of at least one composition effective in reducing a sensitivity of said patient to an asthma associated allergenic reaction wherein the composition comprises a prednisone and at least one of an $H_1$ and an $H_2$ histamines antagonist.

9. The method as recited in claim 8, wherein said pretreatment protocol further comprising administering to said patient at least one of corticosteroid and the leukotriene antagonist.

10. The method as recited in claim 1, wherein said administration step being concurrently repeated using another allergen capable of causing sensitivity in the patient.

11. The method as recited in claim 1, wherein said administering step further includes the step of administering to said patient at intervals of about 15 minutes gradually increasing doses of said allergen each having a dilution level within the range of from between about 1:150,000 to about 1:50,000to between about 1:1500 to about 1:500.

12. A method of treating a patient sensitive to an allergen, comprising a protocol of administering to said patient an effective amount of a composition comprising a series of gradually increasing doses of said composition comprising said allergen at each selected interval being about fifteen minutes for a duration of less than about 120 minutes.

13. The method as recited in claim 12, wherein the dilution level of allergen within each dosage being within the range from between about 1:150,000 to about 1:50,000 to between about 1:1500 to about 1:500.

14. The method as recited in claim 12, wherein said protocol being defined by a dosing schedule consisting essentially of:
   (i) a dosage having about a 1:100,000 allergen dilution level,
   (ii) a dosage having about a 1:100,000 allergen dilution level,
   (iii) a dosage having about a 1:10,000 allergen dilution level,
   (iv) a dosage having about a 1:10,000 allergen dilution level,
   (v) a dosage having about a 1:1000 allergen dilution level, and
   (vi) a dosage having about a 1:1000 allergen dilution level.

15. The method as recited in claim 12, wherein the amount of said composition administered to said patient according to said protocol being therapeutically effective in desensitizing said patient against said allergen.

16. The method as recited in claim 12, wherein said allergen being selected from the group consisting of mold, mildew, dust, and dander.

17. The method as recited in claim 12, wherein said protocol being concurrently repeated using another allergen.

18. The method as recited in claim 12, further comprises a pretreatment protocol of administering to said patient a therapeutically effective amount of at least one composition effective in reducing a sensitivity of said patient to an asthma associated allergenic reaction wherein the composition comprises a prednisone and at least one of the $H_1$ histamine antagonist and an $H_2$ histamine antagonist.

19. The method as recited in claim 18, wherein said prednisone being administered according to a daily dosage of about 60 mg/adult and 2 mg/kg/child.

20. The method as recited in claim 18, wherein said pretreatment protocol being carried out over about three days.

21. The method as recited in claim 18, wherein said $H_1$ histamine antagonist being selected from the group consisting of Loratadine, Terfenadine, Cetirizine hydrochloride, and Fexofenadine hydrochloride, and said $H_2$ histamine antagonist being selected from the group consisting of Ranitidine hydrochloride, Famotidine, and Cimetidine.

22. The method as recited in claim 18, wherein said pretreatment protocol further comprising administering to said patient at least one of corticosteroid and leukotriene antagonist.

23. A method of treating a patient sensitive to an allergen, comprising a protocol of administering to said patient an effective amount of a composition comprising a series of gradually increasing doses of said composition comprising said allergen at intervals of about 15 minutes for a duration of less than about 120 minutes.

24. The method as recited in claim 23, wherein a dilution level of allergen within each dosage being within the range from between about 1:150,000 to about 1:50,000 to between about 1:1500 to about 1:500.

25. The method as recited in claim 24, wherein said protocol being defined by a dosing schedule consisting essentially of:
   (i) a dosage having about a 1:100,000 allergen dilution level,
   (ii) a dosage having about a 1:100,000 allergen dilution level,
   (iii) a dosage having about a 1:10,000 allergen dilution level,
   (iv) a dosage having about a 1:10,000 allergen dilution level,
   (v) a dosage having about a 1:1000 allergen dilution level, and
   (vi) a dosage having about a 1:1000 allergen dilution level.

26. The method as recited in claim 23, wherein the amount of said composition administered to said patient according to said protocol being therapeutically effective in desensitizing said patient against said allergen.

27. The method as recited in claim 23, further comprises a pretreatment protocol of administering to said patient a therapeutically effective amount of at least one composition effective in reducing a sensitivity of said patient to an asthma associated allergenic reaction wherein the composition comprises a prednisone and at least one of an $H_1$ histamine antagonist and an $H_2$ histamine antagonist.

28. The method as recited in claim 27, wherein said pretreatment protocol further comprising administering to said patient at least one of a corticosteroid and leukotriene antagonist.

29. A method for the treatment of an allergic condition to a causative agent by means of desensitization therapy, the treatment method involving a subject sensitive to the causative agent, said method comprising the steps of:
   administering to the subject an effective amount of the causative agent comprising gradually increasing doses of the causative agent; and
   conducting the administration of said causative agent at intervals of between about 10 to 20 minutes for a duration of than about 120 minutes using at each interval a dosage of said causative agent within the range of from between about 1:150,000 to about 1:50,000 to between about 1:1500 to about 1:500.

30. A method of treating a patient sensitive to an allergen, comprising a protocol of administering to said patient an effective amount of a composition comprising a series of gradually increasing doses of said composition comprising said allergen at each selected interval being about fifteen minutes for a duration of less than about 120 minutes, said protocol being defined by a dosing schedule consisting essentially of:
   (i) a dosage having about a 1:100,000 allergen dilution level,
   (ii) a dosage having about a 1:100,000 allergen dilution level,
   (iii) a dosage having about a 1:10,000 allergen dilution level,
   (iv) a dosage having about a 1:10,000 allergen dilution level,
   (v) a dosage having about a 1:1000 allergen dilution level, and
   (vi) a dosage having about a 1:1000 allergen dilution level.

31. The method as recited in claim 30, further comprises a pretreatment protocol of administering to said patient prednisone and at least one of an $H_1$ histamine antagonist and an $H_2$ histamine antagonist.

32. The method as recited in claim 31, wherein said $H_1$ histamine antagonist being selected from the group consisting of Loratadine, Terfenadine, Cetirizine hydrochloride, and Fexofenadine hydrochloride, and said $H_2$ histamine antagonist being selected from the group consisting of Ranitidine hydrochloride, Famotidine, and Cimetidine.

33. The method as recited in claim 31, wherein said pretreatment protocol further comprising administering to said patient at least one of a corticosteroid and leukotriene antagonist.

34. A method of pretreating a patient prior to receiving desensitizing rapid immunotherapy, comprising the steps of:
administering to said patient prednisone and at least one of an $H_1$ histamine antagonist and an $H_2$ histamine antagonist; and
administering to said patient a therapeutically effective amount of at least one composition effective in reducing the sensitivity of said patient to an asthma associated allergenic reaction occurrable during and/or after reception of the desensitizing rapid immunotherapy.

35. The method as recited in claim 34, wherein said at least one composition administered to reduce the sensitivity of said patient to an asthma associated allergenic reaction comprising at least one of a corticosteroid and leukotriene antagonist.

36. A method of pretreating a patient prior to receiving desensitizing rapid immunotherapy, comprising the steps of:
administering to said patient prednisone and at least one of an $H_1$ histamine antagonist and an $H_2$ histamine antagonist; and
administering to said patient at least one of a corticosteroid and leukotriene antagonist.

* * * * *